(12) United States Patent
Spencer

(10) Patent No.: US 8,783,259 B2
(45) Date of Patent: Jul. 22, 2014

(54) ORAL APPLIANCE FOR IMPROVED NOCTURNAL BREATHING

(75) Inventor: Jamison Ross Spencer, Star, ID (US)

(73) Assignee: Cadwell Therapeutics, Inc., Kennewick, WA (US)

(*) Notice: Subject to any disclaimer, the term of this patent is extended or adjusted under 35 U.S.C. 154(b) by 1232 days.

(21) Appl. No.: 12/435,061

(22) Filed: May 4, 2009

(65) Prior Publication Data

US 2009/0272387 A1 Nov. 5, 2009

Related U.S. Application Data

(60) Provisional application No. 61/049,854, filed on May 2, 2008.

(51) Int. Cl.
*A61F 5/56* (2006.01)
*A61C 9/00* (2006.01)

(52) U.S. Cl.
USPC ............. 128/848; 128/859; 128/861; 433/34; 433/37

(58) Field of Classification Search
USPC .......... 128/848, 859, 861–862; 433/6, 34, 37, 433/48; 602/902
See application file for complete search history.

(56) References Cited

U.S. PATENT DOCUMENTS

| | | | |
|---|---|---|---|
| 4,063,552 A | 12/1977 | Going et al. | |
| 4,488,873 A | 12/1984 | Bloomfield et al. | |
| 4,519,386 A | 5/1985 | Sullivan | |
| 4,676,240 A | 6/1987 | Gardy | |
| 4,901,737 A | 2/1990 | Toone | |
| 4,955,393 A * | 9/1990 | Adell | 128/859 |
| 5,082,007 A * | 1/1992 | Adell | 128/861 |
| 5,365,945 A | 11/1994 | Halstrom | |
| 5,381,799 A | 1/1995 | Hamilton | |
| 5,427,117 A | 6/1995 | Thornton | |
| 5,499,633 A | 3/1996 | Fenton | |
| 5,562,106 A | 10/1996 | Heeke et al. | |
| 5,570,704 A * | 11/1996 | Buzzard et al. | 128/848 |
| 5,727,564 A | 3/1998 | Yannalfo | |
| 5,752,822 A | 5/1998 | Robson | |
| 5,794,627 A * | 8/1998 | Frantz et al. | 128/848 |
| 5,816,255 A | 10/1998 | Fishman et al. | |
| 5,846,211 A | 12/1998 | Sakaguchi et al. | |
| 5,846,212 A * | 12/1998 | Beeuwkes et al. | 601/38 |
| 6,050,961 A | 4/2000 | Arnold | |
| 6,263,877 B1 | 7/2001 | Gall | |
| 6,405,729 B1 | 6/2002 | Thornton | |
| 6,494,209 B2 | 12/2002 | Kulick | |
| 7,305,990 B2 | 12/2007 | Mathias | |
| 7,328,705 B2 | 2/2008 | Abramson | |
| 2006/0078840 A1 | 4/2006 | Robson | |
| 2006/0110698 A1 | 5/2006 | Robson | |

(Continued)

OTHER PUBLICATIONS

Instruction Guide, Pure Sleep Product, 2008.

(Continued)

*Primary Examiner* — Patricia Bianco
*Assistant Examiner* — Camtu Nguyen
(74) *Attorney, Agent, or Firm* — Parsons Behle & Latimer

(57) ABSTRACT

An oral appliance includes a one-piece tray system that fits over the posterior teeth of the user and is custom-made or customized using lining material that conforms to the dentition of the wearer. The device may position the lower jaw in a slightly protruded position with respect to the upper jaw.

17 Claims, 10 Drawing Sheets

(56) References Cited

U.S. PATENT DOCUMENTS

| | | |
|---|---|---|
| 2007/0015113 A1 | 1/2007 | Lavi et al. |
| 2007/0079833 A1 | 4/2007 | Lamberg |
| 2007/0224567 A1 | 9/2007 | Robson |
| 2007/0283967 A1 | 12/2007 | Bailey |
| 2007/0292819 A1 | 12/2007 | Scarberry et al. |

OTHER PUBLICATIONS

PCT Search Report from corresponding PCT Application No. PCT/US09/42716, Aug. 24, 2009.

* cited by examiner

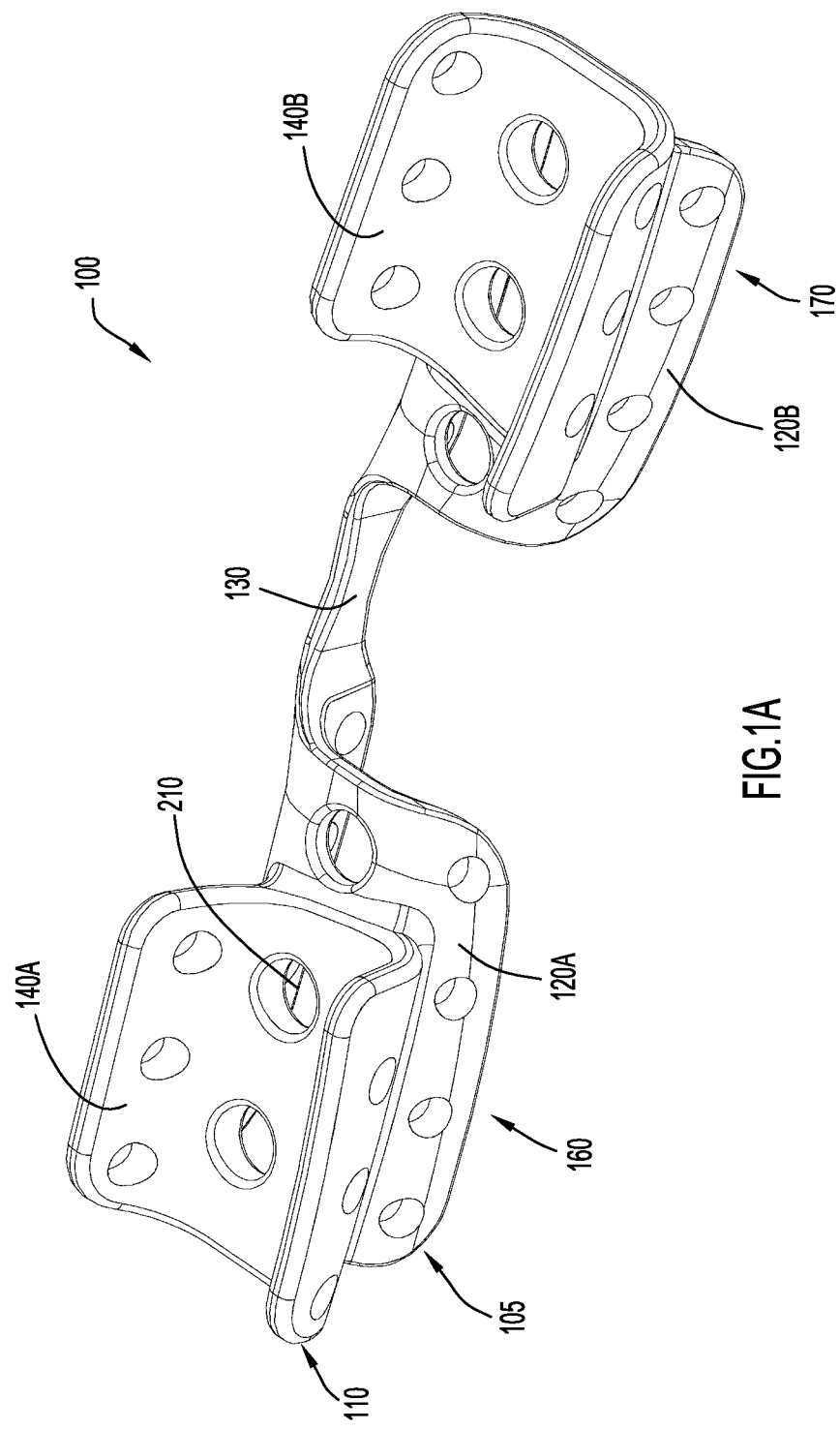

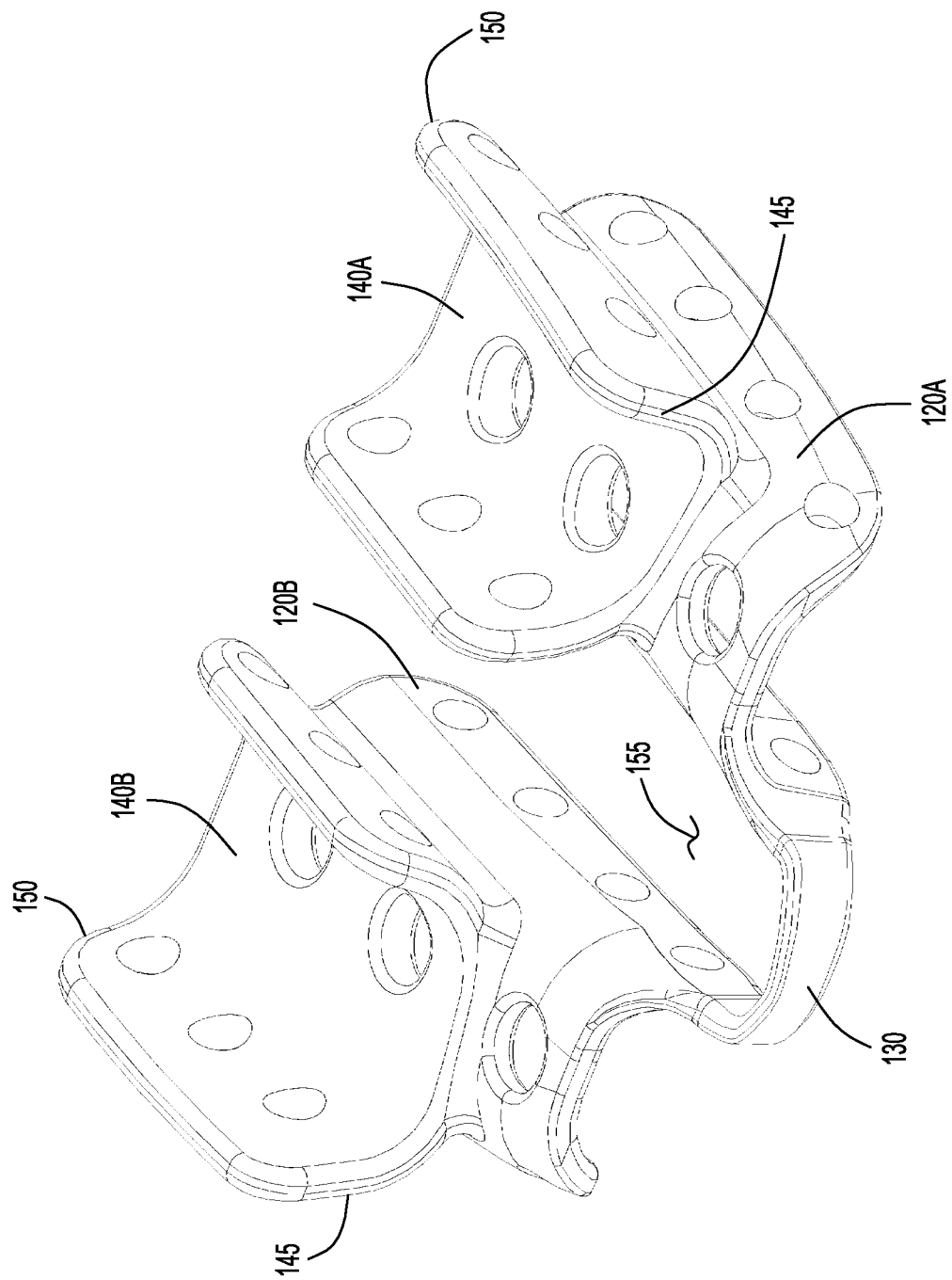

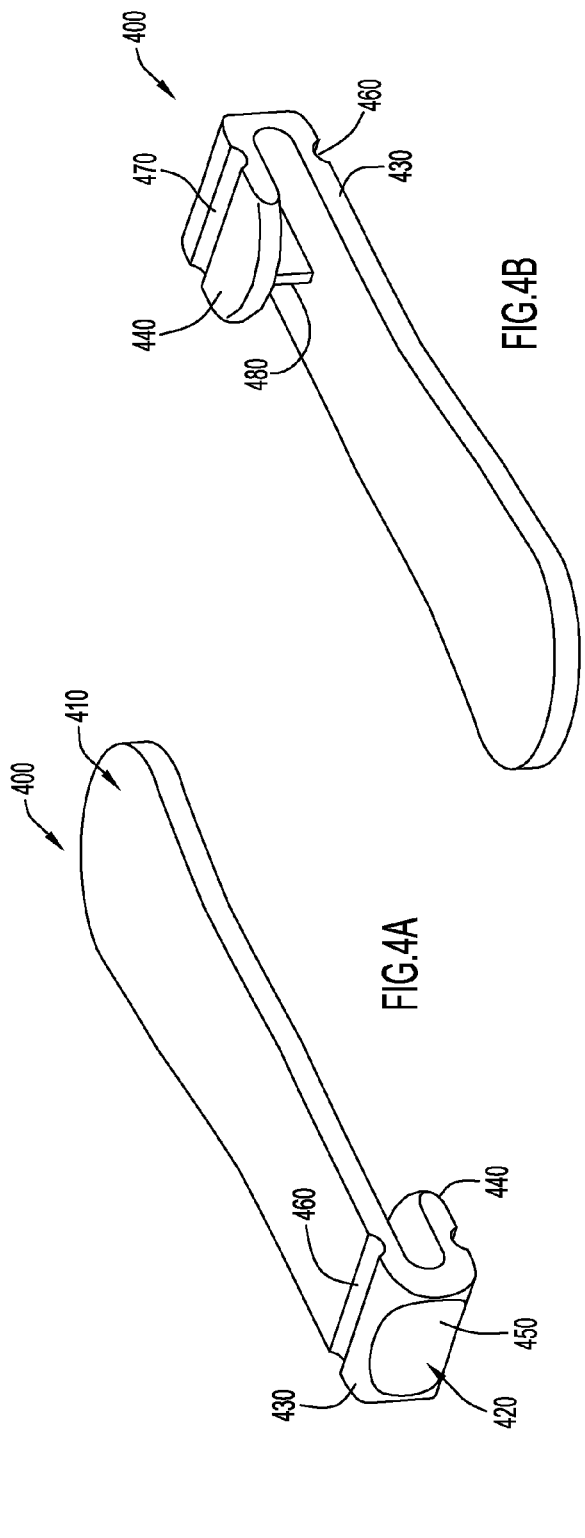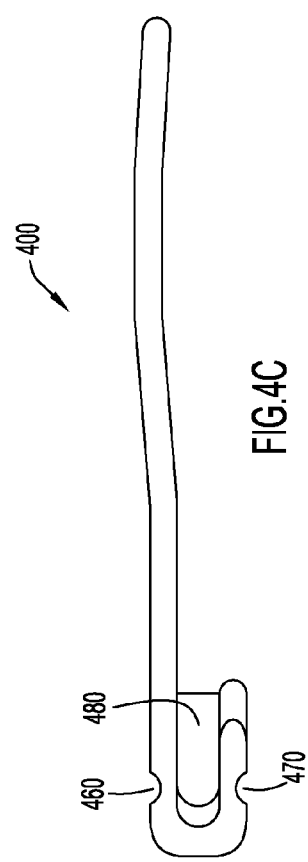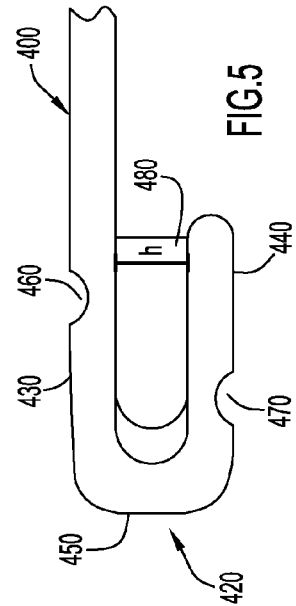

ORAL APPLIANCE FOR IMPROVED NOCTURNAL BREATHING

CROSS REFERENCE TO RELATED APPLICATIONS

This application claims priority to U.S. Provisional Application No. 61/049,854, filed 2 May 2008 and entitled "Oral Appliance for Improved Nocturnal Breathing," the disclosure of which is hereby incorporated by reference in its entirety.

FIELD OF THE INVENTION

The present invention pertains to an oral appliance configured to support a mandible in a predetermined orientation with respect to the maxilla and, in particular, to a dental device including a prefabricated tray and a conforming gel.

BACKGROUND OF THE INVENTION

Many individuals experience difficulty in sleeping because of breathing problems. These difficulties include excessive snoring and the potentially much more serious problem of sleep apnea. Sleep apnea disorders are often treated by the application of constant positive airway pressure (CPAP) delivered to the patient through a face or nose mask. Sleep apnea or snoring conditions can also be successfully treated by dental devices effective for forward extension of the mandible of the patient during sleep. These devices reposition the lower jaw (mandible) in an anterior (forward) direction, pulling the base of the tongue forward and thereby increasing the air passage in the posterior pharyngeal region (breathing passage behind the base of the tongue). This serves to maintain the patient's airway open by preventing the soft tissue of the throat and tongue from collapsing into the airway, thus ameliorating the patient's breathing problems.

Devices that bring the mandible forward into a functional repositioning posture and hold the posterior airway open are currently available. One type of device is manually adjustable, enabling a user to personally adjust the positioning of the device. These devices, however, include many components. As a result, the device takes up a substantial amount of space inside the mouth, which, in turn, limits the amount of space available for the tongue such that the tongue is prevented from coming forward, potentially retarding the flow of air through the patient's airway. In addition, these devices require the dentist or patient to make any necessary adjustments to improve the fit or efficacy of the device. This may also allow adjustments to be made without the guidance of a dentist. Consequently, an improper fit or position may result, which, in turn, results in ineffective treatment for the patient or greater chance of untoward side effects.

In addition, non-adjustable or fixed-position devices are available that are configured to fit within the mouth at a predetermined position. The disadvantage of fixed position devices is that they are not able to be adjusted for improved comfort or efficacy without significant time and expense. Proper placement of the device varies among individual patients. Thus, while the fixed position device may be effective for some, it may not be effective for others. A patient's jaw structure, furthermore, often experiences changes over time. Therefore, the device may require adjustment of the position of the lower jaw in relationship to the upper jaw to remain effective. These devices, not being easily adjustable, cannot accommodate for such changes.

Custom made oral appliances, whether adjustable or non-adjustable also have the disadvantage of having to be lab fabricated requiring impressions of the patient's teeth, creation of stone models, and laboratory expenses. As such, custom made oral appliances tend to be cost prohibitive for many patients.

Pre-fabricated boil and bite devices also exist that require a user (patient or dentist) to submerge the device in boiling water to soften the material lining the device. The user then bites into the device to conform the material to the teeth. This type of device poses safety risks resulting from working with boiling water, as well as the risks associated with placing hot material into the mouth and over the teeth (e.g., intraoral burns and/or pulpal damage). In addition, the material forming the device may not sufficiently conform to the teeth of the user. As a result, an improper fit occurs, causing discomfort to the user and lessening the effectiveness of the device.

Thus, it would be desirable to provide a mandible extension dental device that can be accurately placed within the mouth and can be highly customized to a user, while avoiding the problems associated with the devices described above.

SUMMARY OF THE INVENTION

The present invention relates to an oral appliance for improved nocturnal breathing that is customized for the dentition of the wearer. The appliance includes a pre-fabricated, one-piece tray with receptacles designed to fit over lower and upper posterior teeth. Conformable material may be applied to the interior surface of the receptacles. The lining material cures in situ, becoming anchored to the tray.

In operation, the tray is placed into the mouth of the wearer, and the upper and lower teeth are closed onto the conformable material. The tray is left in place until the material is set. Should the jaw position require adjustment, the cured lining material may be selectively removed and the process performed again with new conformable material. The device is capable of orienting the lower jaw in an anterior position with respect to the upper jaw. The desired degree of protrusion may be determined utilizing a gauge that orients the upper and lower jaws at predetermined positions with respect to each other. The individually fit, prefabricated tray may be used during sleep to improve the patency of the oro-pharyngeal airway, as well as to reduce snoring and/or obstructive sleep apnea.

BRIEF DESCRIPTION OF THE DRAWINGS

FIG. 1A illustrates a top perspective view of an oral appliance in accordance with an embodiment of the invention.

FIG. 1C illustrates a top perspective view of an oral device in accordance with another embodiment of the invention.

FIGS. 4A-4C illustrate a bite gauge in accordance with an embodiment of the invention. Specifically, FIG. 4A illustrates a top perspective view of the bite gauge, FIG. 4B illustrates a bottom perspective view of the bite gauge, and FIG. 4C illustrates a side view in plan of the bite gauge.

FIG. 5 illustrates a close-up view of the measuring end of the bite gauge shown in FIG. 4C.

FIG. 7 is a side view in elevation illustrating the tray dry fit on jaw portions (maxilla and mandible) of a wearer.

FIG. 8 illustrates a top view in perspective, showing the application of the lining material to the tray.

FIG. 9 illustrates a side view in elevation, showing the curing process occurring in situ.

Like reference numerals have been used to identify like elements throughout this disclosure.

DETAILED DESCRIPTION OF THE INVENTION

Figure 1B:
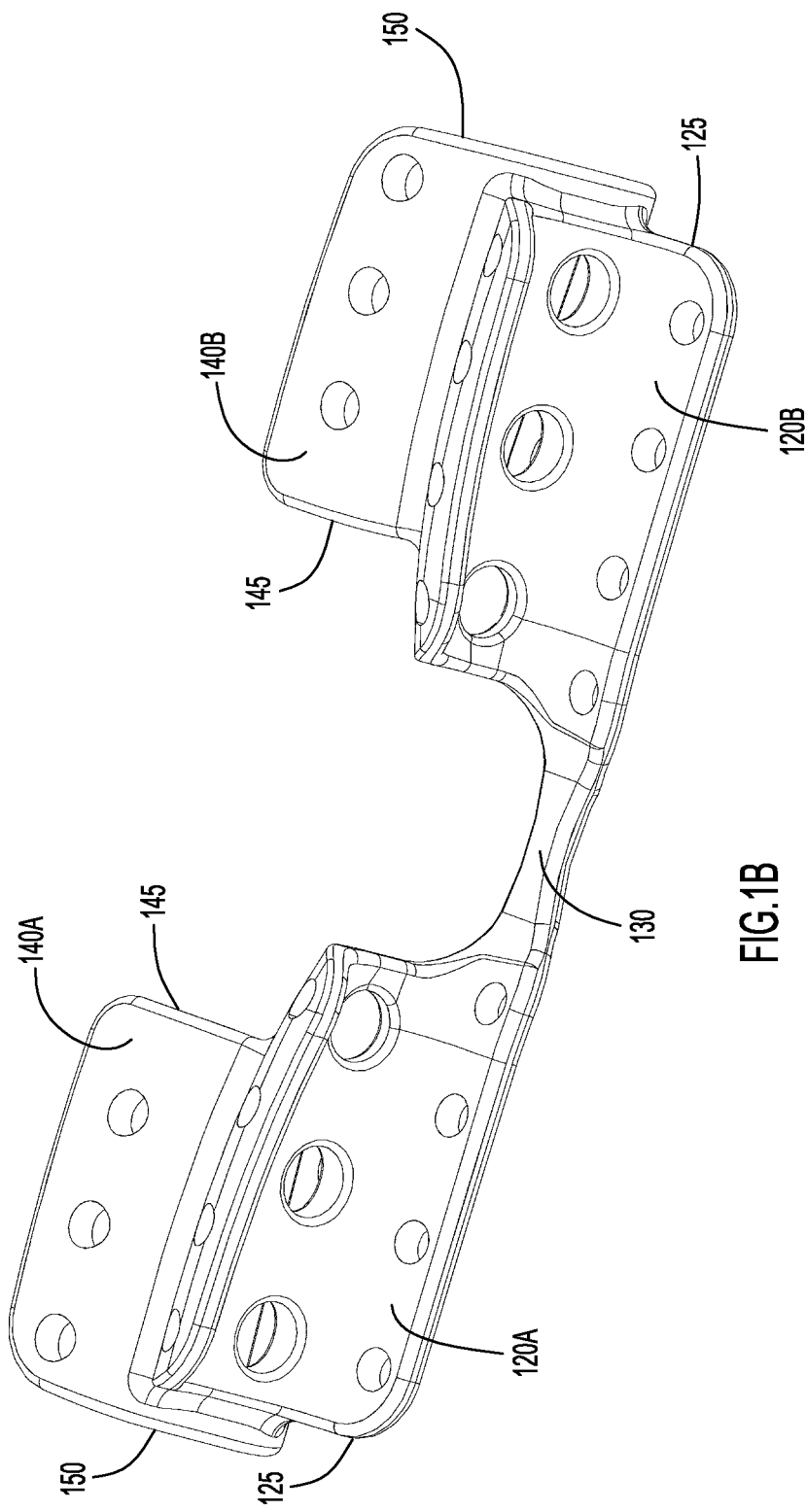
FIG. 1B illustrates a bottom perspective view of the oral of FIG. 1A.

The oral appliance system according to the present invention includes an individually fit, prefabricated tray device and conformable lining (reline) material that is applied to the receptacles of the tray. The tray 100 positions the jaw such that the mandible and maxilla jaw portions are oriented and supported at a predetermined position with respect to each other. Referring to FIGS. 1A, 1B, and 1C, the tray 100 includes a lower or mandibular portion 105 and an upper or maxillary portion 110. The mandibular portion 105 has an open channel configuration, and is operable to receive the posterior teeth of the wearer's lower jaw (e.g., the molars, premolars, and/or canines of the mandible). Specifically, the mandibular portion 105 includes a first mandibular receptacle 120A oriented in spaced relation from a second mandibular receptacle 120B. The receptacles 120A, 120B are preferably substantially mirror images one another, with each receptacle having a generally U-shaped, transverse cross-section. The first mandibular receptacle 120A is coupled to the second mandibular receptacle 120B via an anterior or lingual bridge 130. The anterior bridge 130 may be in the form of a bar interposed between the receptacles 120A, 120B. That is, the first mandibular receptacle 120A extends distally from one end of the bar and the second mandibular receptacle 120B extends distally from the other end of the bar, each receptacle terminating in a distal or posterior end 125. The bar may be connected to the buccal wall/flanges 310, 330 (FIG. 3) of the mandibular receptacles 120A, 120B, being formed integral therewith.

The mandibular receptacles 120A, 120B and bridge 130 may be any shape and possess any dimensions suitable for their described purposes. By way of example, the length of each mandibular receptacle 120A, 120B may be approximately 32 mm, while the length of the bridge may be about 20 mm.

The upper or maxillary portion 110 possesses an opened channel structure configured to receive the upper teeth of the user (i.e., the molars and/or premolars of left and right maxillae). Specifically, the maxillary portion 110 includes a first maxillary receptacle 140A oriented above the first mandibular receptacle 120A and a second maxillary receptacle 140B disposed above the second mandibular receptacle 120B. Receptacles 140A, 140B are preferably substantially mirror images of one another. The first maxillary receptacle 140A is aligned such that its longitudinal axis is generally parallel to the longitudinal axis of the first mandibular receptacle 120A. Similarly, the second maxillary receptacle 140B is aligned such that its longitudinal axis is generally parallel to the longitudinal axis of the second mandibular receptacle 120B. Each maxillary receptacle 140A, 140B may possess a generally U-shaped transverse cross-sectional structure having an anterior end 145 and a posterior end 150 (seen best in FIG. 1C). It should be understood that the maxillary receptacles 140A, 140B may be any shape and possess any dimensions suitable for their described purposes. By way of example, the length of each maxillary receptacle 140A, 140B may be approximately 27 mm.

The resulting tray 100 possesses a left tray subassembly 160, including the first maxillary 120A and mandibular 140A receptacles, and a right tray subassembly 170, including the second maxillary 120B and mandibular 140B receptacles. The receptacles 120A, 120B, 140A, 140B are adapted to contain lining material as described below.

Referring to FIG. 1C, the anterior bridge 130 is configured as an arcuate bar that orients the left 160 and right 170 tray subassemblies generally parallel to each other, forming a generally U-shaped tray bearing all four receptacles 120A, 120B, 140A, 140B. This configuration further creates a structure wherein the mandibular portion 105 and the bridge 130 cooperate to define a lingual opening 155 that accommodates the tongue of the patient/wearer. In operation, the bridge 130 is positioned behind the anterior teeth of the mandible, the mandibular receptacles 120A, 120B are positioned over the posterior teeth of the mandible, and the maxillary receptacles are positioned over the posterior teeth of the maxilla (discussed in greater detail below).

Figure 2:
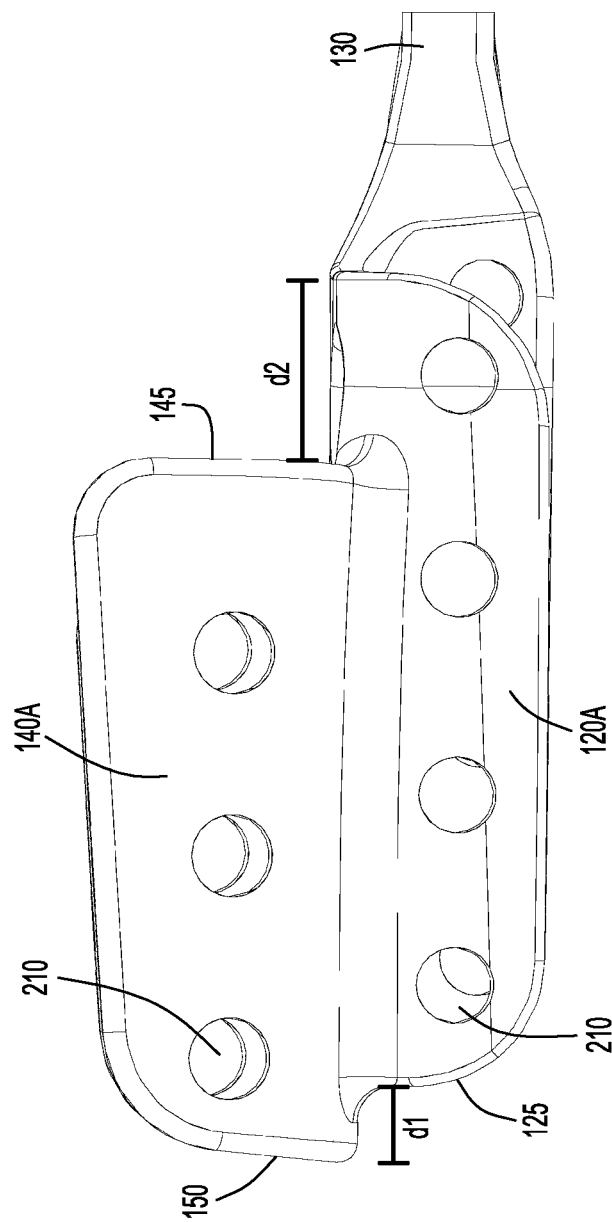
FIG. 2 illustrates a side view of maxillary and mandibular receptacles of a device in accordance with an embodiment of the invention.

Referring to FIG. 2, each maxillary receptacle 140A, 140B may be longitudinally offset from its respective proximate mandibular receptacle 120A, 120B such that only a portion of the receptacles overlap. Specifically, the posterior portion of each maxillary receptacle 140A, 140B may extend beyond the distal edge 125 of its associated mandibular receptacle 120A, 120B by a predetermined distance d1 (and, as such, toward the posterior of the jaw). By way of example, the posterior end 145 of the maxillary receptacle 140A, 140B may extend approximately 6.2 mm beyond the distal end 125 of its corresponding mandibular receptacle 120A, 120B. The proximal portion of the mandibular receptacle 120A, 120B, moreover, may extend a predetermined distance d2 beyond the anterior end 145 of the maxillary receptacle 140A, 140B. By way of example, the proximal portion of the mandibular receptacle 120A, 120B may extend approximately 10 mm beyond the anterior end 145 of the maxillary receptacle 140A, 140B. This offset is desirable in order to provide maximum retention of the tray. As the mandible is brought forward the lower teeth move more anterior in relationship to the maxillary teeth. Thus, the maxillary component is offset posteriorly to accommodate this mandibular shift and allow the tray to cover the upper and lower molars simultaneously. The offset also facilitates flow of the lining material around the posterior of the appliance, connecting the upper and lower material as it sets as a homogenous body. This, in turn, results in greater retention than if the material only went through the retention holes.

Figure 3:
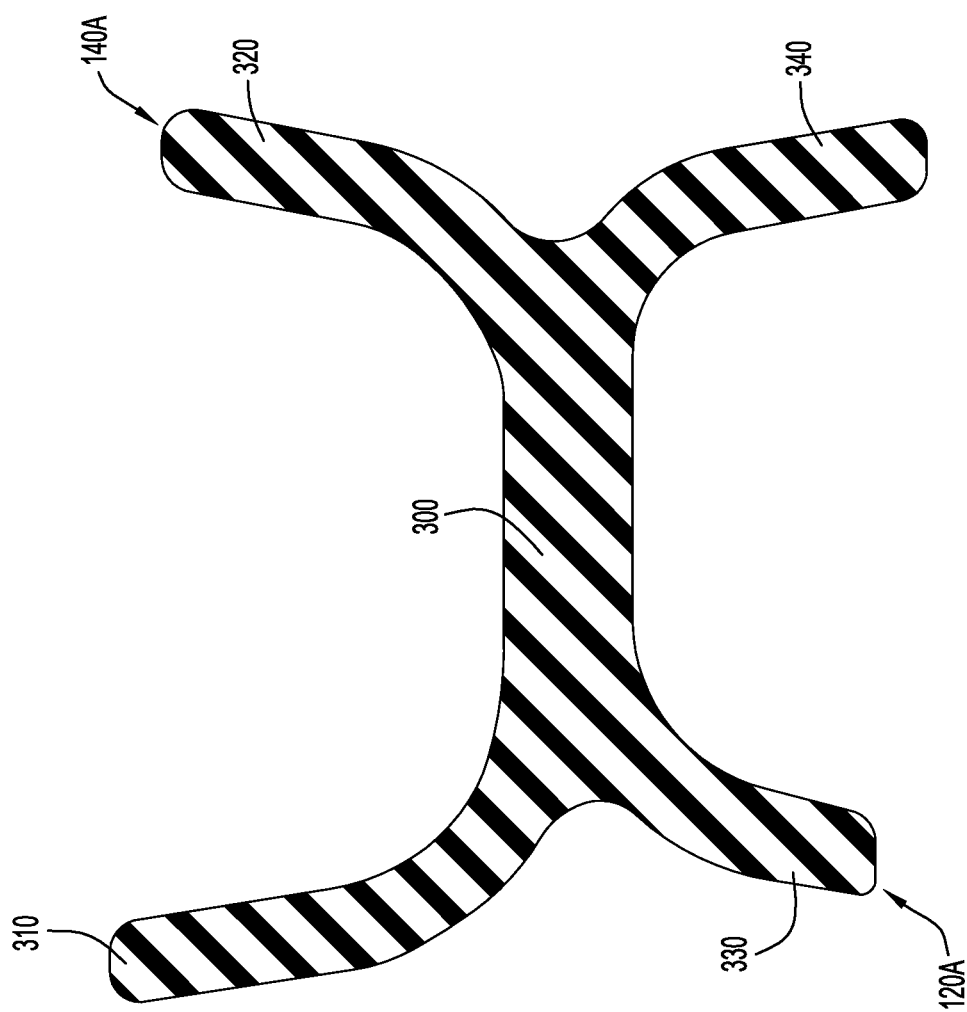
FIG. 3 illustrates a rear view in cross section of a portion of the receptacle shown in FIG. 2.

FIG. 3 is a partial rear cross-sectional view of the tray 100, showing the first mandibular 120A and maxillary 140A receptacles. As shown, the maxillary receptacle 140A possesses a generally U-shaped structure defined by a shared occlusal wall or base 300, an outer or buccal (cheek-facing) flange or wall 310, and an inner or lingual (tongue-facing) flange or wall 320. The proximal portions of the flanges 310, 320 extend from the upper occlusal surface of the base 300 in a generally upward direction. The flanges 310, 320, moreover, curve gently outward as they extend distally from the base 300 and then become straight or substantially linear as they approach their distal ends. The distal edges of each flange 310, 320 may be rounded to increase the comfort for the wearer.

The height of the buccal flange 310 may be greater than the height of lingual flange 320. By way of example, the buccal flange 310 may possess a height of approximately 11.3 mm, while the height of the lingual flange 320 may be about 8.2 mm. The second maxillary receptacle 140B possesses a similar structure, including buccal 310 and lingual flanges 320 as described above.

Similarly, the mandibular receptacle 120A, 120B possesses a generally upside-down, U-shaped structure defined by a buccal (cheek-facing) flange or wall 330 and a lingual (tongue-facing) flange or wall 340, each extending distally from the lower surface of the shared base or occlusal wall 300 in a generally downward direction. As with the maxillary receptacles 140A, 140B, the flanges 330, 340 of the mandibular receptacles 120A, 120B may curve slightly and possess rounded distal edges. The heights of the flanges 330, 340, moreover, may differ. For example, the height of the lingual flange 340 may be greater than the height of the buccal flange 330. By way of specific example, the height of the lingual flange 340 may be about 8.25 mm (measured from surface of the base), while the height of the buccal flange 330 may be about 6 mm (measured from surface of the base).

The walls of the receptacles 120A, 120B, 140A, 140B are shaped to maximize tongue space and allow for support of the reline material and ultimately retention of the fit appliance. Thus, the receptacle 140A, 140B of the maxillary portion 110 of the tray 100 are shorter on the palate (lingual) side and longer on the buccal side. The receptacle 120A, 120B of the mandibular portion 105 is shorter on the buccal and longer on the palate (lingual) side. This conforms to the specific oral anatomy of the respective areas and makes for a more comfortable tray while maintaining retentive features. With this configuration, the receptacles 120A, 120B 140A, 140B accommodate the contours of the teeth and gum line, providing a secure, yet comfortable fit for the posterior teeth of the maxilla.

The buccal flanges 310, 330 and lingual flanges 320, 340 are slightly resilient. That is, while generally rigid, the flanges 310, 320, 330, 340 may be configured to flex slightly to accommodate lateral movement of the jaws and provide greater patient comfort. The flanges 310, 320, 330, 340 may possess any suitable shape or dimensions suitable for the function described. For example, the flanges 310, 320, 330, 340 may possess a thickness of approximately 2 mm. The transverse dimension of maxillary receptacles 140A, 140B (measured from interior surfaces of walls) may be approximately 18 mm. The transverse dimension of mandibular receptacle 120A, 120B (measured from interior surfaces of walls) may be approximately 15 mm. The thickness of the base 300 may be about 2 mm. The thickness of the base 300 along overlapping receptacles may possess a thickness of about 4 mm in the overlapping regions.

This configuration, a lower and upper tray attached with a lower lingual bar and free of material covering the anterior teeth, allows for maximum tongue space and the ability of the treating dentist to easily establish a therapeutic position. The occlusal wall 300 may possess a constant thickness. Alternatively, the thickness of the occlusal wall 300 may vary. By way of specific example, the occlusal wall 300 may taper from front to back (or vice versa) The receptacles 120A, 120B, 140A, 140B, then, may be configured to be thinner in the posterior allowing for reduced vertical dimension of occlusion along the posterior jaw area.

Referring back to FIG. 2, each tray portion 105, 110 may include a plurality of apertures or retention holes that function as anchor points for the lining material described below. The apertures 210 may be longitudinally spaced at predetermined locations along each of the buccal flange 310, 320 and the lingual flange 330, 340 of the receptacles 120A, 120B, 140A, 140B. Similarly, one or more apertures 210 may be formed into the base 300 such that a through-hole is created in the base. For example, as best seen in FIGS. 1A and 1B, a pair of apertures 210 is aligned with the longitudinal axis of each receptacle base 300. The apertures 210 in the base 300 of the tray 100 enable extend from the maxillary receptacle 140A, 140B to the mandibular receptacle 120A, 120B (e.g., the lining material may flow through the aperture, or may be manually urged through the aperture). This, in turn, allows the lining material to set as a homogenous unit that is bound together through the base 300. The apertures 210, then, allow the lining material to extrude through and mechanically bond with the tray upon setting.

The positioning of the apertures 210 is not particularly limited. By way of example, the center axis of apertures in the buccal flange 310, 330 and lingual flange 320, 340 may be located approximately 4 mm from the surface of base 300. Similarly, the shape and dimensions of the apertures 210 may be any suitable for their described purpose. By way of example, the apertures 210 may possess a generally circular shape having a diameter of 2.5-4.0 mm (e.g., 3.25 mm). Providing the tray 100 with apertures having smaller diameters may decrease the ability of the lining material to bond with the tray 100. Providing the tray with apertures 210 of larger diameters, in contrast, may decrease the overall strength of the tray 100.

Additionally, the interior surface of the receptacles 120A, 120B, 140A, 140B may be textured to further improve the adhesion of the lining material to the tray 100. The exterior surface of the tray 100 may be smooth for maximum comfort of the wearer.

The tray 100 possesses a unitary (one-piece) structure formed of a resilient material such as thermoplastic. By way of example, the appliance may be formed of polyether-based thermoplastic polyurethane (e.g., IROGAN A 85 P 4394 R, Huntsman Polyurethanes, The Woodlands, Tex., USA). The tray 100 may be formed utilizing conventional injection molding processes. The Shore (Durometer) Hardness of the material 100 may be any suitable for its described purpose. By way of example, the resulting tray 100 may possess a Shore (Durometer) Hardness, Shore A, of 75-95.

The conformable lining material is bio-compatible material that initially conforms to the contours of the tray and the dentition of the wearer, but hardens into a generally nonconforming structure. By way of example, the conformable material may be dental reline material, dental impression material, dental acrylics, dental composites, dental bite registration materials, and or other dental materials. Dental reline material (e.g., dental reline) is generally preferred due to its strength, resilience, and modulus of elasticity. By way of specific example, the conformable material may be material curable by temperature, radiation (UV light), etc. By way of example, the conformable material may be a vinyl polysiloxane, such as a cold cure vinyl polysiloxane (e.g., GC Reline Material, GC Coporation, Tokyo, Japan, 510K # K990736). It should be understood, however, that any vinyl polysiloxane material compatible with the tray 100 may be utilized. In addition, polyether, silicone, rubber base, and other dental impression or bite registration materials could also be utilized. Other lining materials that could be utilized with the tray 100 include a cold cure acrylic, a heat cure acrylic, thermally active acrylics (tone polymer), composites (self cure or light cure), or other similar materials. Once hardened, the lining material, which has infiltrated apertures 210, becomes anchored to the tray 100.

In operation, the lining material is applied to the inner surface of the receptacles 120A, 120B, 140A, 140B. The tray 100 is positioned in the mouth of the patient, where the lining material hardens in situ (e.g., while in contact with the teeth of the wearer). As the lining material sets, the lining material conforms to the contours of the teeth, as well as to the contours of soft tissues (tongue, cheek, and gingival tissues), providing a customized fit (discussed in greater detail below).

As noted above, the tray 100 is configured to support the jawbone such that the maxillary teeth and the mandibular teeth are oriented in relative positions. Specifically, the tray 100 distances the anterior teeth of a mandible from those of the maxilla to open the oro-pharyngeal airway. The term "spacing" includes vertical separation (called the vertical dimension of occlusion) as well as horizontal spacing (called the horizontal or differential dimension), in which the mandible is moved forward or rearward with respect to the maxilla (e.g., to create an overbite or an under bite).

The maxillary-mandibular position (vertical or horizontal spacing) may be measured and/or set utilizing a bite gauge device such as the one illustrated in FIGS. 4-5. In the embodiment shown, the bite gauge device 400 possesses a generally J-shaped structure defined by an elongated handle or gripping member 410 and a distal teeth-engaging or measuring portion 420. The handle 410 may be generally planar. Alternatively, the handle 410 may be angled with respect to the teeth-engaging portion 420 (seen best in FIG. 4C). The teeth-engaging portion 420 defines a generally U-shaped structure including a first arm or component 430 and a second arm or component 440 connected via an arcuate medial portion 450. The first arm 430 includes a first exterior groove 460 and the second arm 440 includes a second exterior groove 470 defined therein. These exterior grooves 460, 470 extend generally transversely in the gauges and are configured to receive the anterior teeth of the jaw. By way of example, the first exterior groove 460 may receive the anterior teeth of the maxilla, while the second exterior groove 470 receives the anterior teeth of the mandible (or vice versa). To this end, the grooves are typically linear; however, grooves having a slight curvature may be employed.

The location of the first and second exterior grooves 460, 470 may be set at predetermined positions along their respective arms 430, 440. By way of example, the first exterior groove 460 may be aligned with the second interior groove 470 (FIG. 4C). Alternatively, the first exterior groove 460 may be offset from the second exterior groove 470 at a predetermined distance (FIG. 5). That is, the grooves 460, 470 may be longitudinally spaced at measured positions along the device 400. By way of example, one gauge 400 may have the first exterior groove 460 spaced approximately 2 mm from the second exterior groove 470, while another gauge may have the first exterior groove spaced approximately 4 mm from the second exterior groove.

Figure 6A:
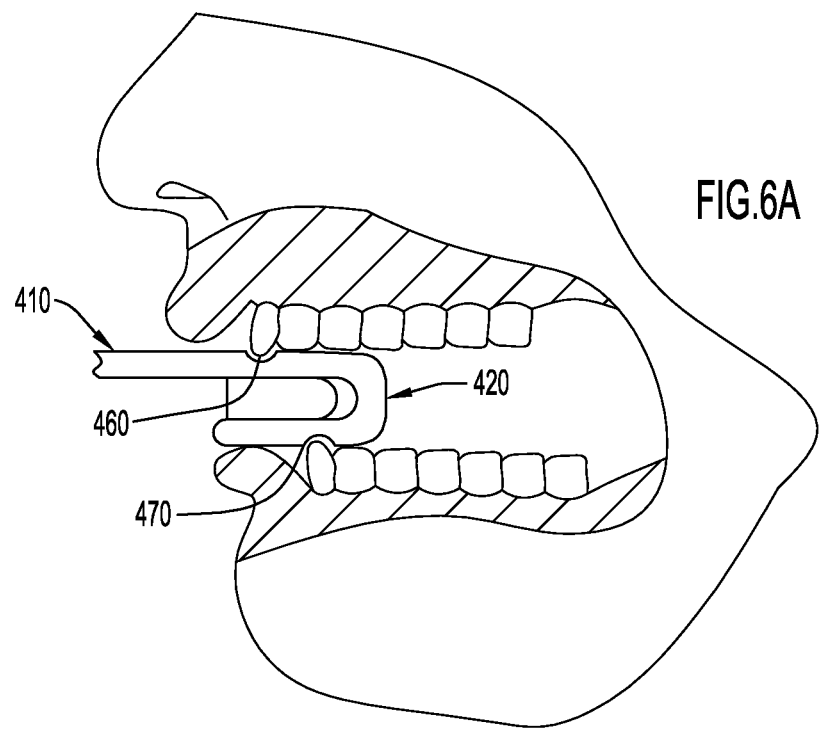
FIGS. 6A and 6B illustrate side views in elevation illustrating the operation of the bite gauge shown in FIG. 4A.
Figure 6B:
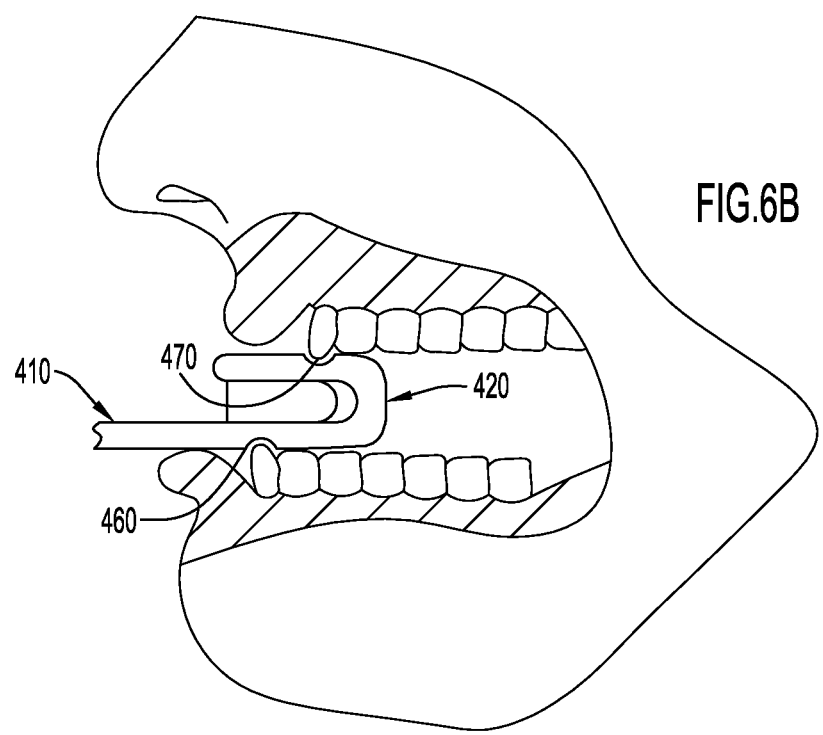

The gauge 400 may be utilized to measure the natural maxillary-mandibular positioning of a patient. In addition, the gauge 400 may be utilized to establish a desired maxillary-mandibular position and/or maintain the position during curing of the reline material. The operation of the bite gauge 400 is explained with reference to FIGS. 6A and 6B. In operation, the handle 410 is grasped and the teeth-engaging portion 420 is inserted into the mouth. The teeth-engaging portion 420 is positioned such that one of the grooves 460, 470 aligns with the anterior teeth of the mandible (or vice versa). To obtain the measurement of the patient's bite (and establish the differential dimension), the patient is instructed to bite down onto the gauge 400. Should the anterior teeth of the maxilla align with the opposite groove, the differential between the maxilla and mandible is determined since the spacing between the grooves has a known value. If the teeth do not align with the grooves, the gauge 400 is removed and repeated with additional gauges having different groove locations until alignment is achieved.

To establish the maxillary-mandibular position, the gauge 400 is positioned within the mouth as described above. The patient is instructed to adjust the relative position of the mandible until the anterior teeth of each jaw portion align with the groove. Once the teeth become positioned within the grooves, the maxillary-mandibular measurement is established.

Since a series of bite gauges 400 may be configured with varying spacing between the first and second grooves 460, 470, different mandibular positions may be accomplished. That is, when the grooves are offset, the position of the lower jaw can be positioned forward of the upper jaw (FIG. 6B) or behind the upper jaw (FIG. 6A), depending on how the bite gauge 400 is held. If the upper groove is posterior to the lower groove, this will require a protruded position of the mandible. If the same bite gauge 400 is turned over, this relationship will be reversed. Stated another way, each bite gauge 400 includes offset grooves 430, 440 that can be utilized to establish two different maxillary-mandibular positions. For example, a bite gauge 400 having a 2 mm offset between grooves 460, 470 would allow for 2 mm of protrusion relative to the upper jaw or 2 mm of retrusion relative to the upper jaw, depending on how the bite gauge 400 was oriented.

The vertical dimension of occlusion can also be set utilizing the bite gauge 400. Referring back to FIG. 5, the medial portion 450 spaces the first arm 430 from the second arm 440 by a predetermined distance h. Thus, alteration of the dimensions of the medial portion 450 and/or the thickness of the arms 430, 440 may be used to adjust this height h. Increasing or decreasing the height h respectively increases or decreases the vertical dimension of occlusion. In addition, a spacer 480 may be inserted between the arms 430, 440 to provide the desired height h. That is, providing a spacer with a greater height increases the value of h.

Figure 7:
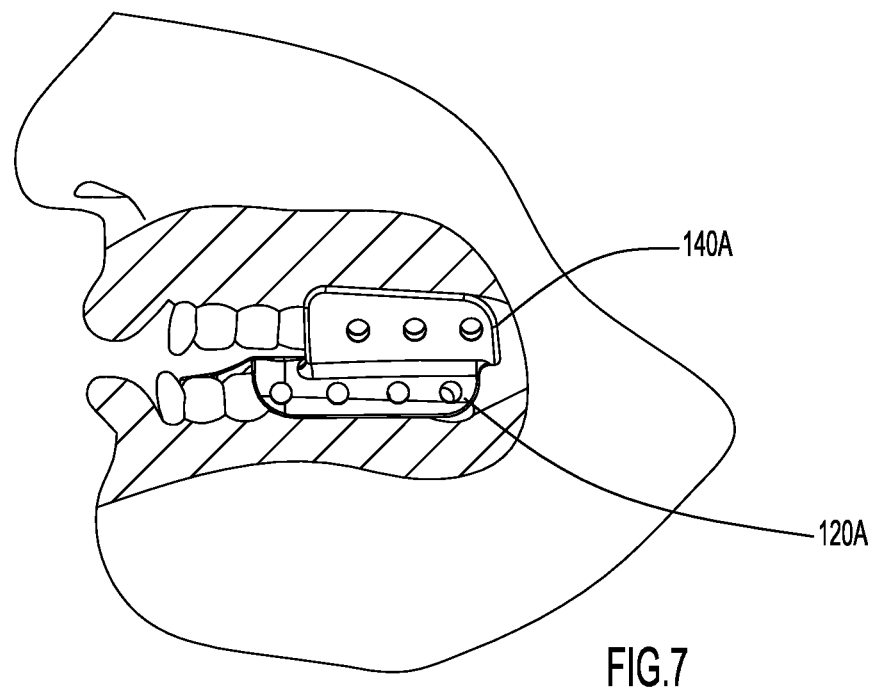
FIGS. 7-9 illustrate the operation of the device of FIG. 1C. Specifically.
Figure 9:
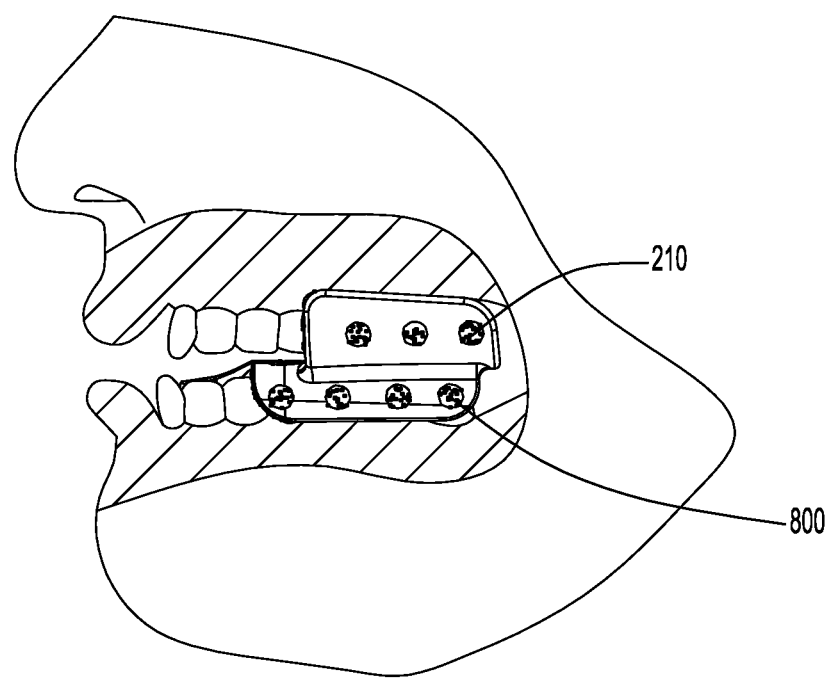

The operation of the oral appliance is explained with reference to FIGS. 7-10. The maxillary-mandibular position may be determined utilizing the bite gauge 400 as described above. Referring to FIG. 7, the tray 100 is dry fitted (i.e., without the lining material) onto the teeth to determine sizing and comfort of the unlined tray. By way of example, the tray 100 should be able to fit over the wearer's posterior teeth (molars and/or premolars) without interference or painful contact with the soft or hard tissues. The bridge 130 is positioned such that it rests behind the lower anterior teeth of the wearer.

Figure 8:
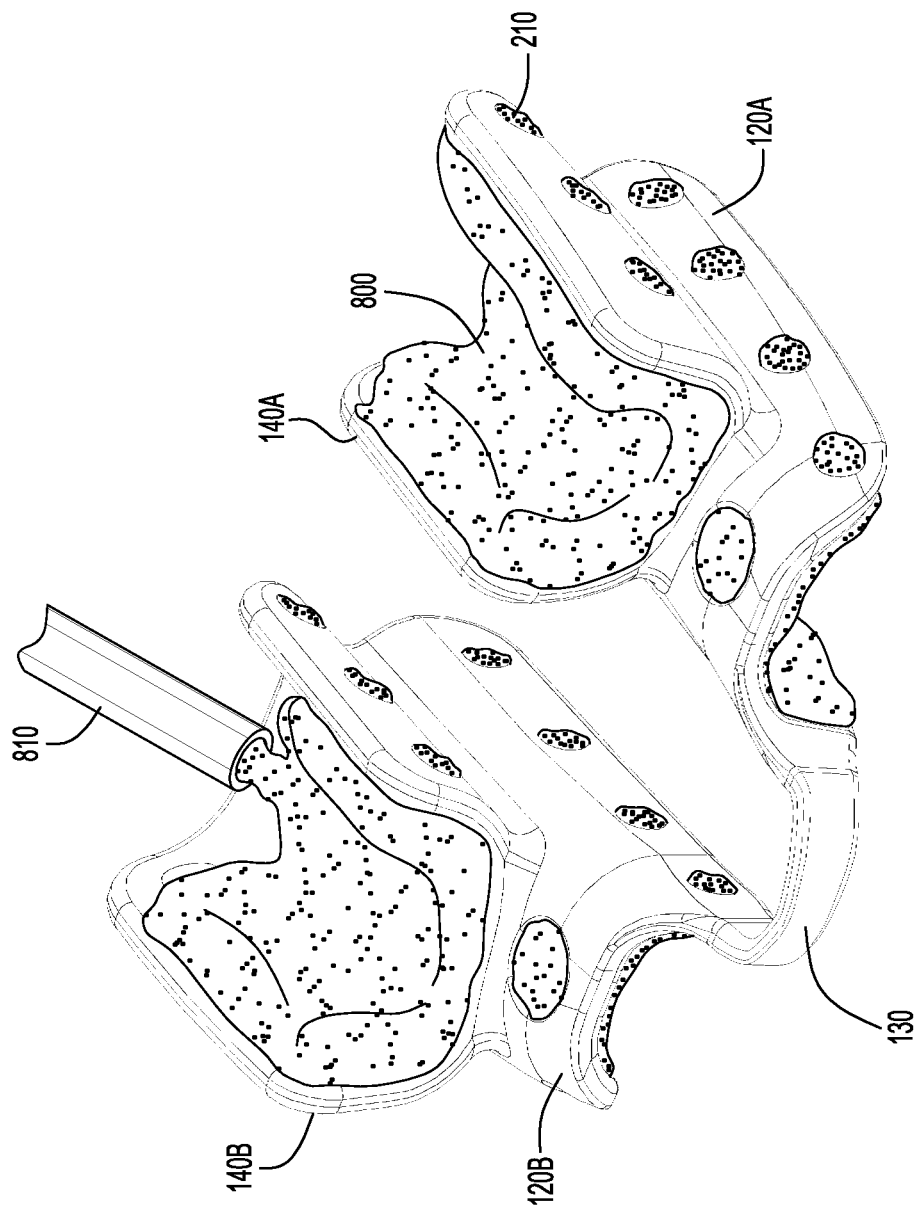
Figure 10:
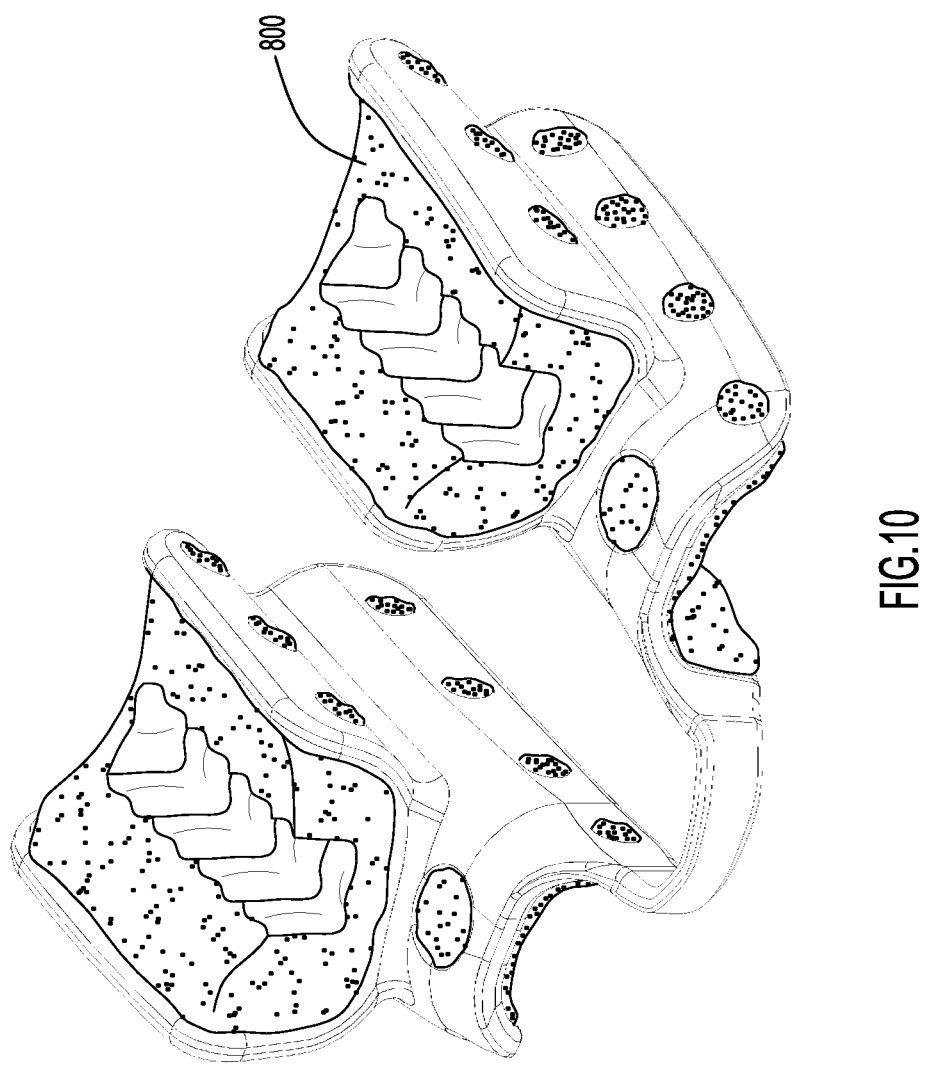
FIG. 10 illustrates a top view in perspective, showing the formed appliance, with the lining material conforming to the dentition of the wearer.

Referring to FIG. 8, the tray 100 is removed from the wearer's mouth (e.g., by grasping the bridge 130), and the lining material 800 is applied to receptacles 120A, 120B, 140A, 140B. By way of example, the cold-cure vinyl polysiloxane material may be injected via a syringe 810 such that the material coats the interior surface of the receptacles 120A, 120B, 140A, 140B, traveling into and/or through the apertures 210 located along the occlusal 300, buccal flanges 310, 330, and lingual flanges 320, 340. Alternatively, when a vinyl polysiloxane putty impression material is utilized, the impression material is kneaded and then placed onto the interior surfaces of the receptacles, urging the putty through the apertures 210. As noted above, other dental materials may be utilized following typical protocols and manufacturer instructions.

Once the tray 100 is lined with the lining material 800, the tray is returned to the wearer's mouth (FIG. 9), being guided such that the mandibular portion 105 is positioned onto the mandibular posterior teeth and located at the previously determined position obtained during the dry fit. The wearer then bites down into the lined tray 100, using the bite gauge 400 as previously described or another method to establish the maxillo-mandibular position. The lining material 800 is allowed to cure/set, depending on the material utilized. For example, some materials set within three minutes. Other materials may take at least five minutes to set. Once fully set, the tray 100 is removed from the mouth of the wearer. Any excess material may be trimmed (e.g., material flowing outside of the receptacles 120A, 120B, 140A, 140B) to eliminate area that could cause irritation to soft tissues or easily separate from the tray. The tray 100 may then be returned to the wearer's mouth to confirm wearer comfort. The resulting tray 100 is now customized for the wearer, with the cured lining material forming a negative mold of the wearer's dentition (seen in FIG. 10).

The tray device 100 achieves the beneficial result of opening the oro-pharyngeal airway by several different mechanisms. The device keeps the wearer's mandible from moving posteriorly during sleep. As mentioned above, during sleep, the jaw will naturally fall back due to reduced muscle tone and gravity (when the patient is supine), which may result in the narrowing or obstruction of the airway due to the tongue and other soft tissues collapsing. The tray 100 helps to maintain oro-pharyngeal patency by supporting the jaw from falling back during sleep. In addition, the device 100 results in increased muscle tone in the oro-pharyngeal muscles and the tongue, which further helps to maintain the opening of the airway. The tray 100 allows for maximum space in the anterior of the appliance so as not to restrict the tongue from moving forward or cause the tongue to have to retract back into the throat. By way of specific example, the vertical distance between at least a portion of the posterior teeth may be at least about 4 mm (i.e., the thickness of the base along overlapping receptacles 120A/140A, 120B/140B). In a preferred embodiment, the vertical spacing provided by the tray positions the jaw such that an opening exists in the anterior that is sufficient to allow the patient's tongue to slightly protrude between the anterior teeth, unrestricted.

The tray 100, furthermore, may be configured such that it positions the mandible forward of its normal position to further increase the oro-pharyngeal airway. This may be accomplished by having the patient physically protrude the mandible forward while the lining material sets. In one embodiment, the protrusion is achieved via the bite gauge 400 as described above. Specifically, the bite gauge 400 is utilized to establish the maxillary-mandibular positioning while the lining material is curing in situ.

As noted above, the tray 100 covers the lower and upper posterior teeth (an, in some cases, the canines), with the bridge 130 resting behind the user's lower anterior teeth. This configuration allows for maximum space for the tongue when compared to devices that cover the anterior teeth or have a connection bar that crosses the palate. Conventional appliances cover the anterior teeth, which reduces the amount of space for the tongue and, as such, reduces the ability of the device to move the tongue out of the airway.

The oral appliance of the present invention provides several advantages of prior art appliances. The trays 100 of the current system are reusable and may be selectively adjustable. For example, should the tray 100 cause the patient discomfort, the cured lining material 800 may be removed by applying sufficient manipulative force to extract the material from the receptacles 120A, 120B, 140A, 140B. A new measurement utilizing the bite gauge 400 may optionally be performed, and a new layer of lining material 800 may then be applied as described above. Thus, the position of the tray 100 on the mandible/maxilla may be adjusted to obtain a more comfortable bite pattern (to increase or decrease the degree of jaw protrusion) or, if the current jaw protrusion is ineffective, to adjust it to a more effective position. Use of this method of customization allows the appliance to also be used in patients who are still growing or used in patients who are in braces. In such case, a custom-fabricated appliance cannot typically be used since it may restrict growth. In addition, a "boil and bite" appliance is cannot be used in a patient fit with orthodontic appliances.

The resulting oral appliance provides a custom fit to a wearer, increasing the effectiveness of the appliance while maintaining maximum comfort. The tray 100 per se, not being formed of "boil and bite" material, cannot generally be custom fitted to the teeth and gums of the wearer. The lining material 800 filled into the receptacles 120A, 120B, 140A, 140B, however, provides customization similar to so called "boil and bite" appliances, but eliminates the dangers associated with boiling the appliance and placing the hot material into the mouth and providing a much better fit and function. In addition, since the non-custom tray and the lining material are both made from resilient/flexible material, the device allows for dampening of forces placed on the teeth and jaws during sleep in people who clench and/or grind their teeth (bruxism).

The device also improves upon previous designs of oral appliances by, among other things, maximizing tongue space through minimization of material in the anterior of the appliance and connecting the posterior aspects of the tray using a lingual bar on the lower rather than in the palate. The fitting method and design of the appliance allow for maximum tongue space through minimizing material in the anterior of the appliance and connecting the posterior aspects of the appliance with a lingual bar resting behind the mandibular teeth rather than in the palate.

While the invention has been described in detail and with reference to specific embodiments thereof, it will be apparent to one skilled in the art that various changes and modifications can be made therein without departing from the spirit and scope thereof. For example, the tray may be of any size or any suitable dimensions. The material forming the tray 100 or the lining material 400 is not particularly limited. While the tray 100 is preferably formed from material that is not a boil-and-bite type material, such a material may be utilized to form the conformable material 800.

In addition, the tray portions 105, 110 may be completely custom fabricated with the above-described design intended to maximize tongue space. That is, the receptacles 120A, 120B, 140A, 140B may individually or collectively be preformed to the dentition of the wearer. A hybrid appliance could also be fabricated such that lower portion of the tray is custom fabricated to the user's teeth but the upper portion is fabricated in such a way that it may be relined in order to vary and adjust the mandibular position as previously described with the pre-fabricated, non-customizable tray embodiment. By way of example, a mold of the maxilla may be used to create a maxillary portion 110 customized to the dentition of the maxilla. The receptacles of the mandibular portion 105, however, may be customized in situ utilizing the conformable material 800 as described above. By way of further example, the mandibular receptacles 120A, 120B may be preformed, and the maxillary receptacles 140A, 140B may be formed in situ utilizing the conformable material as described.

The flanges 310, 320, 330, 340 may be formed from materials providing varying levels of flexibility. The apertures 210 may be present in any number/concentration, and may possess any shape and dimensions suitable for their described purpose. For example, instead of a circular shape, the apertures 210 may possess a polygonal shape. The overall shape and dimensions of the tray 100 is not particularly limited. By way of example, the overall length of the tray 100, measured along the occlusal wall 300, may be approximately 96.4 mm. The bite gauge 400 may be utilized to establish the maxillary-mandibular position for the fitting of a direct oral appliance or for registration of an occlusal record for fabrication of a custom made oral appliance. The bite gauge 400 may be used in tandem with the tray 100 or may be utilized independently from the tray. The bite gauge 400 may be formed from stiff or flexible material (e.g., metal, plastic, glass, etc.).

Thus, it is intended that the present invention cover the modifications and variations of this invention that come within the scope of the appended claims and their equivalents. It is to be understood that terms such as "left", "right" "top", "bottom", "front", "rear", "side", "height", "length", "width", "upper", "lower", "interior", "exterior", "inner", "outer" and the like as may be used herein, merely describe points of reference and do not limit the present invention to any particular orientation or configuration.

I claim:

1. An oral appliance for positioning the mandibular portion of the jaw with respect to the maxillary portion of the jaw, the oral appliance comprising a unitary tray including:
    a mandibular portion comprising:
        a first mandibular receptacle,
        a second mandibular receptacle oriented in spaced relation from the first mandibular receptacle, and
        a bridge member coupling the first mandibular receptacle to the second mandibular receptacle, wherein the first and second mandibular receptacles receive mandibular teeth; and
    a maxillary portion comprising:
        a first maxillary receptacle operable to receive maxillary teeth, wherein the first maxillary receptacle is coupled to the first mandibular receptacle;
        a second maxillary receptacle operable to receive maxillary teeth, wherein the second maxillary receptacle is coupled to the second mandibular receptacle;
        a first aperture formed in the first mandibular receptacle and the first maxillary receptacle, wherein the first aperture is defined by a through-hole providing fluid communication between the first mandibular receptacle and the first maxillary receptacle; and
        a second aperture formed in the second mandibular receptacle and the second maxillary receptacle, where the second aperture is defined by a through-hole providing fluid communication between the second mandibular receptacle and the second maxillary receptacle.

2. The oral appliance of claim 1, wherein the maxillary receptacles are offset from the mandibular receptacles such that each maxillary receptacle extends beyond a posterior edge of its associated mandibular receptacle.

3. The oral appliance of claim 2, wherein each mandibular receptacle extends beyond an anterior edge of its associated maxillary receptacle.

4. The oral appliance of claim 1, wherein:
    the tray comprises an occlusal base wall having first occlusal surface and a second occlusal surface opposite the first occlusal surface;
    the mandibular receptacles comprise:
        a buccal flange extending from the first occlusal surface, and
        a lingual flange extending from the first occlusal surface, wherein the mandibular receptacle forms an open channel; and
    the maxillary receptacles comprise:
        a buccal flange extending from the second occlusal surface, and
        a lingual flange extending from the second occlusal surface, wherein the mandibular receptacle forms an open channel.

5. An oral appliance for opening the oro-pharyngeal airway of a wearer, the oral appliance comprising a unitary tray including:
    a mandibular receptacle operable to receive mandibular teeth;
    a maxillary receptacle operable to receive maxillary teeth; and
    an aperture for retention of lining material, the aperture extending through both the mandibular and maxillary receptacles,
    wherein the oral appliance supports a mandible such that it is vertically spaced from the maxilla and opens the oro-pharyngeal airway of the wearer,
    wherein the maxillary receptacle is offset from the mandibular receptacle such that the maxillary receptacle extends beyond a posterior edge of the mandibular receptacle to define a shoulder.

6. The oral appliance of claim 5 further comprising a plurality of apertures for retention of lining material, at least one aperture being formed into the shoulder.

7. The oral appliance of claim 5, wherein the aperture for retention of lining material is a through-hole aperture configured to retain the lining material in a homogenous unit by creating a mechanical bond of lining material via the through-hole aperture to the mandibular and maxillary receptacles.

8. A dental system for opening the oro-pharyngeal airway of a wearer, the system comprising:
    a generally rigid tray having a unitary structure, the tray comprising:
        a mandibular receptacle operable to receive mandibular teeth;
        a maxillary receptacle operable to receive maxillary teeth; and
        an aperture for retention of lining material; and
    lining material operable to cure from a conformable state to a non-conformable state, wherein the maxillary receptacle is offset from the mandibular receptacle such that an anterior end of the mandibular receptacle extends beyond an anterior end of the maxillary receptacle to define a shoulder and wherein the aperture defines a through-hole extending from the mandibular receptacle to the maxillary receptacle; and the lining material extends through the aperture to mechanically connect to the tray.

9. The dental system of claim 8 further comprising a bite gauge including: a first groove operable to receive mandibular anterior teeth; and a second groove operable to receive maxillary anterior teeth.

10. The dental system of claim 9, wherein the first groove is offset from the second groove to align the maxillary anterior teeth forward or rearward of the mandibular anterior teeth.

11. The dental system of claim 10, wherein the bite gauge device comprises:
    a handle portion to permit manipulation of the device; and
    a teeth-engaging portion defined by a first wall, an arcuate medial portion, and a second wall, wherein the first groove is formed in an exterior surface of the first wall and the second groove is formed in an exterior surface of the second wall.

12. The dental system of claim 11, wherein:
the first and second walls define a gap;
the bite gauge device further comprises a spacer disposed within the gap and between the first and second walls; and
the spacer maintains the spacing between the walls.

13. The dental system of claim 8, wherein:
the tray comprises an occlusal base wall having first occlusal surface and a second occlusal surface opposite the first occlusal surface;
the mandibular receptacle comprises:
   a buccal flange extending from the first occlusal surface, and
   a lingual flange extending from the first occlusal surface; and
the maxillary receptacle comprises:
   a buccal flange extending from the second occlusal surface, and
   a lingual flange extending from the second occlusal surface.

14. A method of adjusting the positioning of mandible with respect to the maxilla, the method comprising:
(a) obtaining an oral appliance comprising unitary tray including:
   a mandibular receptacle operable to receive mandibular teeth,
   a maxillary receptacle operable to receive maxillary teeth, and
   an aperture for retention of conformable material, the aperture extending through both the mandibular and maxillary receptacles, wherein the maxillary receptacle is offset from the mandibular receptacle such that an anterior end of the mandibular receptacle extends beyond an anterior end of the maxillary receptacle to define a shoulder and wherein the aperture for retention of conformable material is a through-hole aperture configured to retain the conformable material in a homogenous unit by creating a mechanical bond of conformable material via the through-hole aperture to the mandibular and maxillary receptacles;
(b) applying a curable reline material to the receptacles of the oral appliance;
(c) filling the aperture of the oral appliance with conformable material;
(d) curing the reline material to solidify the material; and
(e) positioning the oral appliance within the mouth of a wearer.

15. The method of claim 14, wherein (d) comprises:
(d.1) positioning the dental appliance into the mouth of the wearer;
(d.2) positioning maxillary teeth within the maxillary receptacle;
(d.3) positioning the mandibular teeth within the mandibular receptacle; and
(d.4) curing the reline material while in contact with the teeth such that the material conforms to the dentition of the wearer.

16. The method of claim 15, further comprising:
(f) positioning a bite gauge between the anterior teeth of the maxilla and the anterior teeth of the mandible, the bite gauge including:
   a first groove operable to receive mandibular anterior teeth; and
   a second groove operable to receive maxillary anterior teeth;
(g) positioning the anterior teeth of the mandible within the first groove; and
(h) positioning the anterior teeth of the maxilla within the second groove, wherein the bite gauge engages the anterior teeth during the curing of the reline material.

17. The method of claim 14, wherein (b) further comprises (b.1) directing the curable material through the aperture.

\* \* \* \* \*